United States Patent [19]

Parks

[11] 4,295,987
[45] Oct. 20, 1981

[54] CROSS-LINKED SODIUM POLYACRYLATE ABSORBENT

[75] Inventor: Lawrence R. Parks, Cincinnati, Ohio

[73] Assignee: The Procter & Gamble Company, Cincinnati, Ohio

[21] Appl. No.: 106,958

[22] Filed: Dec. 26, 1979

[51] Int. Cl.$^3$ .................. B01J 20/04; D21D 3/00; B01J 20/10; B01J 20/26
[52] U.S. Cl. .................. 252/194; 162/168 R; 162/168 NA; 428/147; 428/301; 428/318; 428/339; 428/264; 525/363; 525/366; 526/81; 526/86; 526/123; 526/130; 252/429 B; 252/449
[58] Field of Search ............ 252/194, 429 B, 449; 162/168 R, 168 NA; 428/147, 301, 318, 339, 264, 534, 535; 525/363, 366; 526/81, 86, 101, 102, 123, 130

[56] References Cited

U.S. PATENT DOCUMENTS

| | | | |
|---|---|---|---|
| 3,235,610 | 2/1966 | Wymorp | 252/194 |
| 3,293,683 | 12/1966 | Wyant | 428/535 |
| 3,366,582 | 1/1968 | Adams et al. | 521/84 |
| 3,679,621 | 7/1972 | Morf et al. | 162/168 R |
| 3,686,024 | 8/1972 | Nankee et al. | 428/264 |
| 4,090,013 | 5/1978 | Ganslaw et al. | 526/81 |

*Primary Examiner*—Benjamin R. Padgett
*Assistant Examiner*—Irwin Gluck
*Attorney, Agent, or Firm*—Fredrick H. Braun; Richard C. Witte

[57] ABSTRACT

The present invention involves compositions of super absorbent polymers which absorb many times their weight in water and aqueous fluids. Super absorbent polymers in the prior art have effectively absorbed many times their weight of water, however, they become slimy to the touch or become so fluid as to migrate away from their point of application.

The absorbent composition of the current invention absorbs substantial amounts of water without becoming slimy and migrating out from its applicator, as in absorbent articles. The absorbent composition of the current invention comprises a copolymer of acrylic acid cross-linked with a first cross-linking component comprising a monomer having at least two vinyl groups and a second cross-linking component comprising an ionic divalent cation. In the current invention, this composition can be mixed with cellulose fibers to enhance wicking. This composition is useful in absorbent articles and has proven to be particularly well suited to be incorporated between two plies of paper to make a two-ply paper towel.

18 Claims, No Drawings

CROSS-LINKED SODIUM POLYACRYLATE ABSORBENT

TECHNICAL FIELD

This invention relates to absorbent polymeric materials in particular to absorbent polymeric materials useful in absorbent articles.

In formulating absorbent polymeric materials for use in household absorbent articles it is important that the absorbent material absorb many times its weight in water, that the material not become slimy (i.e., maintain a high viscosity) when it has absorbed the water and not migrate from the article in which it is placed. It is essential that the absorbent material hold the water absorbed under pressure and that the absorbent material maintain its cross-linked polymeric construction and not be dissolved in high pH or low pH cleaning solutions used with cleaning articles. The composition disclosed may also be used in absorbent structures such as diapers or catamenials.

BACKGROUND ART

The background art teaches a variety of polymeric absorbent materials. U.S. Pat. No. 4,090,013 issued to Ganslaw et al. on May 16, 1978 teaches a water absorbent polymer for use in absorbent diapers or dressings. The absorbent in Ganslaw is a three component polymer having a long chain neutralized polyacrylic acid polyelectrolyte; chain extenders of di-functional monomers such as allyl methacrylate; and trivalent metal cations complexing and cross-linking the long chain polyelectrolytes.

Compositions using zinc are taught in the Background Art: U.S. Pat. No. 3,959,237 issued to Blank on May 25, 1976; U.S. Pat. No. 4,066,584 issued to Allen on Jan. 3, 1978; and U.S. Pat. No. 3,404,134 issued to Rees on Oct. 1, 1968.

British Pat. No. 869,333, published on May 31, 1961 of Rohm & Haas Company discloses acrylic polymers cross-linked with divalent calcium ions added as calcium acetate and alkali metal salt of methacrylic or acrylic acid.

Use of vinyl cross-linking agents is taught in U.S. Pat. No. 3,157,623 issued to Braun on Nov. 17, 1964. Use of triethylene glycol dimethacrylate as a cross-linking compound to increase gel viscosity in ethyl acrylate polymers is taught in the article by Stephen L. Rosen, "Some Rheological Properties of a Linear-Gel Polymer System", No. 7, APPLIED POLYMER SYMPOSIA, 127–141 (1968).

Absorbent articles containing an absorbent polymer are taught in U.S. Pat. No. 3,686,024 issued to Nankee et al. on Aug. 22, 1972 and U.S. Pat. No. 3,366,582 issued to Adams et al. on Jan. 30, 1968.

Grafting of acrylic acid to cellulose is taught in U.S. Pat. No. 3,457,198, issued to Sobolov on July 22, 1969.

DISCLOSURE OF THE INVENTION

The absorbent composition of the present invention comprises acrylic acid cross-linked with a first cross-linking component comprising a monomer having at least two vinyl groups and a second cross-linking component comprising an ionic divalent cation.

The composition of the current invention can include a copolymer which contains up to 50% by weight of a second monomer selected from the group consisting of methacrylic acid, 2-hydroxyethyl methacrylate, acrylamide, and acrylic acid esterfied with a primary alcohol containing from 1 to about 9 carbon atoms (hereinafter acrylic esters).

Disclosed herein is a process to make the absorbent composition of matter disclosed herein. A container is supplied with a first mixture of acrylic acid; a cross-linking monomer having at least two vinyl groups; a polymerization initiator; and water. The contents of the container are mixed in a nitrogen atmosphere at 40° C.–80° C. for approximately one hour to yield a first mixture. The first mixture is maintained at 40° C.–80° C. for approximately two hours and is subsequently neutralized to yield a second mixture. An ionic divalent cation is added to the second mixture and mixed to yield a composition of the current invention.

Disclosed herein is an absorbent device having a carrier means, such as a sheet of paper, and an absorbent composition applied to the carrier means comprising a copolymer of acrylic acid cross-linked with a first cross-linking component comprising a monomer having at least two vinyl groups and the second cross-linking component comprising an ionic divalent cation.

DESCRIPTION

One aspect of this invention is an absorbent composition or, as described hereinafter, an absorbent copolymer.

The absorbent copolymer of this invention comprises acrylic acid, a cross-linking monomer, and a cross-linking agent. The absorbent copolymer can contain other optional monomeric species.

Preferably, acrylic acid comprises from about 47 to about 90% by weight of the absorbent copolymer and most preferably from about 85 to about 90% by weight.

The cross-linking monomer must include at least two vinyl groups within the molecule. Specific examples of suitable cross-linking monomers include the more water soluble diacrylates such as, for example, ethylene glycol diacrylate and tetraethylene glycol diacrylate as well as diacrylamides such as, for example, methylene-bis-diacrylamide. The cross-linking monomer is present in the absorbent copolymer at from about 1 to about 35% by weight of the copolymer, preferably from about 1 to about 15%.

The cross-linking agent is a divalent cation. Examples of suitable divalent cations include zinc, calcium, strontium, and barium. In practice, the divalent cation is incorporated into the absorbent copolymer through the agency of a salt such as, for example, an acetate. The divalent cation is present in the absorbent copolymer at a level of from about 3 to about 30% by weight of the copolymer, preferably, from about 6 to about 25% by weight.

The optional monomeric species is selected from the group consisting of methacrylic acid, 2-hydroxyethyl methacrylate, acrylamide, esters of methacrylic acid having the following formula:

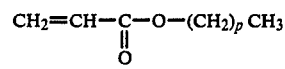

wherein p has a value of from 0 to 8, and mixtures thereof. The optional monomeric species may be present at levels up to about 50% by weight of the absorbent copolymer. Preferably, the absorbent copolymer does not contain any optional monomeric species.

In a preferred embodiment, the acid groups of the absorbent copolymer have been neutralized, preferably with alkali metal hydroxide and most preferably with sodium hydroxide.

In a preferred embodiment, the absorbent copolymer comprises from about 86 to about 89% acrylic acid, from about 1 to about 2% tetraethylene glycol diacrylate, and from about 10 to about 12% zinc divalent cation. The preferred absorbent copolymer has a molecular weight of from about 10,000 to about 10,000,000 and preferably from about 250,000 to about 500,000.

In an especially preferred embodiment, the absorbent copolymer can be represented by the structural formula:

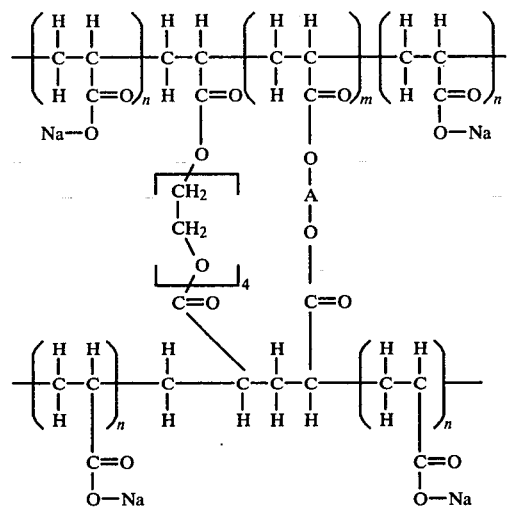

wherein n is from about 100 to about 500, m is approximately 1 to about 30, and A is a divalent cation selected from the group consisting of zinc, calcium, strontium, barium, and mixtures thereof.

The structure of the formula above is an exemplary embodiment having a structure that is 2 weight percent tetraethylene glycol diacrylate and yielding a structure having n=500 and m=30.

The composition disclosed herein absorbs large amounts of liquid without experiencing gel blocking. Gel blocking occurs when particles absorb liquid on their surface and swell to prevent passage of liquid into the center of the particle for additional absorption. The divalent cation cross-linker binds the long chain acrylic acid polymers to prevent the surface swelling which impedes absorption.

In the preferred embodiment, the divalent cation is zinc. Zinc acetate dihydrate is added at a level of 20 to 45 weight percent of the copolymer and preferably 35 to 40 weight percent of the copolymer. When zinc acetate dihydrate is added, zinc will itself comprise 6 to 30 weight percent of the composition and preferably 10 to 12 weight percent of the composition.

The composition disclosed herein can be made by the following method. The following materials are placed in a nitrogen atmosphere in a one liter reaction vessel equipped with a stirrer, condenser and maintained at a temperature of 40°-80° C. in a water bath: acrylic acid; 0 to 50% by weight of the total polymer of a fourth component selected from the group consisting of methacrylate acid, 2-hydroxyethyl methacrylic, acrylamide, and acrylic esters with methyl to nonyl ester groups; a divinyl monomer, such as tetraethylene glycol diacrylate; a polymerization initiator such as potassium persulfate; and water. The contents of the vessel are stirred by the stirrer for about one hour until a thick gel forms as a first mixture. Polymerization continues without stirring for approximately two hours at 40°-80° C. After three hours of total reaction time, the gelatinous product is removed from the reaction vessel and placed in a blender. The gel is blended with a solution of sodium hydroxide and water to form a second solution that is substantially neutralized. After about thirty minutes, a solution of a divalent cation cross-linker and water is blended and reacted with the second mixture in the blender to yield a third mixture. The third mixture is then dehydrated with excess methanol until a firm solid is formed. This solid is dried in a vacuum oven at 60° C. until dry (about 8 hours for 25 gm).

In the process to make the composition disclosed herein, gel stiffness of the final product can be varied by varying amount and type of divinyl cross-linker used. In the most preferred embodiment of the invention, a 2 weight percent level of divinyl cross-linker is preferred to reduce the cost of cross-linker needed and to produce a soft, easily handled gel.

An example of the process to make the preferred composition disclosed herein is seen in Example I below.

EXAMPLE I

The following materials were placed in a nitrogen atmosphere in a one liter reaction vessel equipped with a stirrer, condenser and nitrogen inlet held in a water bath at 60° C.:

18.75 g acrylic acid
0.375 g tetraethylene glycol diacrylate
0.1 g potassium persulfate
170.0 g water The contents of the reaction vessel were mixed by the stirrer for one hour to yield a first mixture. The first mixture was then allowed to sit as polymerization continued for two hours without mixing. After three hours of total reaction time, the gelatinous product formed was removed to a blender and neutralized by adding a solution of 20.85 g of 50% sodium hydroxide in 25 ml. of water to yield a second mixture. After blending the second mixture for thirty minutes, a solution of 18.75 g of zinc acetate dihydrate in 100 ml. of water, was blended with the second mixture in the blender to yield a third mixture. The contents in the blender were mixed yielding a final product which was dehydrated with one gallon (3.785 liters) of 100% methanol which produced a solid. The solid was dried in a vacuum oven at 60° C. for about eight hours.

In the above noted process, the second mixture can be washed, dried and stored. The second mixture can then be reswollen by adding water and the divalent cation cross-linker mixed in to yield the composition described herein.

The composition disclosed herein can be made with different divalent cations or mixtures thereof. The divalent cation cross-linker that is the component of this composition may be zinc, calcium, strontium, barium or mixtures thereof.

Calcium can be used as a divalent cation when mixed with the polymer as calcium acetate. Where calcium acetate comprises another embodiment of the invention, calcium is divalent cation A in the structure above comprising 3 to 8 weight percent and preferably 6 to 7 weight percent of the final copolymer.

Strontium can also be used as the divalent cation A in the above structural formula. When strontium is used as a divalent cross-linker, it comprises from 8 to 18 weight percent and preferably 10 to 16 weight percent of the final absorbent composition. Strontium is added to the copolymer as strontium acetate at 19 to 42 weight percent and preferably 24 to 38 weight percent of the copolymer.

Barium can also be the divalent cation used in the composition disclosed herein as the cross-linker A in the structural formula above. When barium is used as a divalent cation in the composition, it comprises 12 to 28 weight percent and preferably 16 to 25 weight percent of the final composition. Barium is added to the polymer as barium acetate at 22 to 52 weight percent and preferably 30 to 46 weight percent of the copolymer.

In another embodiment of the composition disclosed herein ground cellulose pulp is added to the absorbent composition disclosed herein. The added cellulose pulp functions as both an absorbent and a wicking aid to draw water into the center of the absorbent composition. The use of ground pulp improves overall copolymer efficiency by distributing liquid for absorption within the composition itself.

The composition disclosed herein can be used in any application wherein a highly absorbent material is required to absorb liquids without becoming slimy. Because of the low cost of the composition of the current invention, it is particularly desirable for use in disposable absorbent products.

The composition disclosed herein is particularly useful when combined in a cleaning article. The composition of the current invention is well adapted to be used in a cleaning article used with a cleaning fluid having a high pH solution. The composition disclosed herein is not appreciably soluble in solutions having a pH from as low as 1 to as high as 14. The acrylic acid cross-linked with the divinyl cross-linkers is not pH sensitive because the divinyl cross-linkers are not affected by a high pH solution. Therefore, articles used with a cleaning fluid incorporating the compositions of the current invention are particularly useful as the absorbent composition will not break down or solubilize to migrate out of the article onto the surface being cleaned.

When the composition is combined in a towel, the towel will absorb more liquid, at a faster rate and will hold the liquid better under pressure than a towel not containing the composition.

A preferred embodiment of a paper towel incorporating the absorbent composition disclosed herein is a two ply paper towel with a powdered absorbent composition contained and secured in place between two plies of paper. A method to construct a towel containing the absorbent composition is to apply powdered absorbent composition to a first ply of paper by any of the following means: grinding the composition into a powder and air laying the composition on a paper sheet placed across the inlet of a vacuum box; grinding the absorbent composition into a powder and shaking the powder on a moving ply of paper from a shaking trough; grinding the composition into a powder and applying powder to the first ply of paper through a grooved or perforated roll; or any other conventional means used to apply a powdered substance to a sheet of paper. An agent for bonding together paper sheets is then applied to the first ply of paper either along with the powdered composition or applied directly to the first ply and will hold the second ply to the first ply with a powdered composition therebetween. The second ply of paper is then applied on top of the first ply of paper with the powdered composition therebetween and bonded by conventional means to the first ply.

In a less preferred embodiment, the powdered absorbent composition disclosed herein is applied to a single ply of paper in a moistened form. Upon drying, the absorbent will adhere to the single ply.

An example of a process to make the paper towel containing the absorbent composition disclosed herein is described below.

EXAMPLE II

An eleven inch square (70.97 cm$^2$) first sheet of tissue paper made according to the method taught in U.S. Pat. No. 3,301,746 issued to Sanford et al. on Jan. 31, 1967 having a basis weight of 16 pounds per 3,000 square feet (7.2 Kg per 276 square meters) was placed on a screen on top of a vacuum source and a current of air was drawn through the sheet. A bonding agent, 0.75 gms of polyethylene fibers (Crown Zellerbach E790 available from Crown Zellerbach Corp., San Francisco, California), was added to the air stream and the fibers were equally distributed onto the surface of the paper sheet.

The above described absorbent composition can be dried and mixed with 20 to 50% cellulose pulp fibers. The resulting pulp-polymer mixture is subsequently ground to pass through a 40 mesh screen.

Next, 0.25 grams of the powdered pulp-polymer composition is added to the air stream and subsequently deposited by the air stream on the surface of the first paper sheet. A second sheet of the same paper was superimposed over the first sheet to enclose and secure the polymer powder and polyethylene fibers between the two sheets. The two plies were sealed together by pressing them between the heated platens of a hydraulic press. The heated platens had matching diamond-shaped patterns which melted the polyethylene fibers along the lines of the diamonds. The platens were heated to a temperature of 300° F. (149° C.) and applied a pressure of 2,000 PSI gage (140.69 Kg/cm$^2$) to the sheets therebetween. The two plies were secured together by the melted polyethylene fibers. The resulting product was a two ply towel having a layer of absorbent polymer therebetween.

In the above disclosed two-ply embodiment of the paper towel containing the composition disclosed herein, the plies of paper act as both an absorbent and a carrier for the absorbent composition. It is most desirable to have the absorbent composition carried on a paper rather than being incorporated in a fibrous paper structure, such as a towel paper matrix. In such a system, the most desirable operating characteristics in an absorbent composition-towel system results when there is the least physical interaction between the absorbent composition and the fibers of the paper sheets. Intermixing of cellulose fibers of a paper substrate and wet polymers which are subsequently dried result in a combination of the absorbent polymer tightly wrapped around the cellulose fiber of the paper. In a system with the polymer wrapped around the fiber, the polymer is impeded in its ability to absorb water and expand resulting in a product with a relatively low rate of absorption, although yielding a high final absorbed volume of aqueous solutions. A lower rate of absorption would make a polymer system undesirable on a towel because the rate of absorption would be too slow for the use intended. However, such a product would be useful in a device wherein a slow absorption rate is acceptable, i.e., catamenials.

A paper towel containing the new compositions disclosed herein shows improved performance in that it picks up significantly more water than a paper without the absorbent composition. Spill wipe-up (water) data shown in Table I illustrates the increased absorbency of a towel containing the composition disclosed herein. In Table I, TCV is a "Task Completion Volume" which measures the amount of water wiped up by a towel before leaving a visible amount of water on a given surface after wiping. In the method of measuring TCV, 10 cc of water is poured on a resin saturated cellulose surface such as Formica (Formica is a trademark of Formica Corporation, 120 E. Fourth Street, Cincinnati, Ohio) and wiped up with a dry two ply paper towel being tested. Increments of 2.5 cc of water are then added and wiped up until the towel becomes wet and leaves visible wet streaks on the surface such that it will no longer wipe the surface dry. The amount of water picked up before streaking is TCV.

The absorbent composition in the towel is sodium polyacrylate cross-linked with 2% by weight tetraethylene glycol diacrylate and 12% by weight zinc. The amount of absorbent composition in the towel is "Absorbent Composition in the Sheet" of Table I.

TABLE I

| Absorbent Composition in the Sheet (Grams) | TCV (cc) |
|---|---|
| 0 (Blank) | 20 |
| 0.075 | 22.5 |
| 0.150 | 27.5 |
| 0.225 | 27.5 |
| 0.300 | 30.0 |
| 0.450 | 32.5 |

The increased absorbency of a paper towel containing the composition disclosed herein is illustrated in Table II. Table II shows the increase in the Vertical Full Sheet Absorption (VFS) resulting from the increased amounts of the absorbent composition in a two ply paper towel.

The Vertical Full Sheet Absorption Test determines the amount of water absorbed by a two ply paper towel in carefully controlled measuring conditions. The towel contains given amounts of the absorbent composition comprising sodium polyacrylate, 2% by weight of tetraethylene glycol diacrylate and 12% by weight zinc. The amount of the absorbent composition contained in the two-ply towel is listed in the column entitled "Absorbent Composition in the Sheet". The towel is measured to determine its dry weight. The towel is then placed horizontally on a rack and held in place by loose netting on either side to prevent floating of the towel. The towel and rack are then lowered horizontally into a reservoir of distilled water for a period of 30 seconds. The towel is then removed from the water and allowed to drain horizontally for 160 seconds, shifted to a vertical position and allowed to drain for an additional 60 seconds. The wet towel is removed and weighed to determine the amount of water retained. The VFS Absorption was measured for two separate two ply towel samples. The results are listed in the columns entitled "Sample 1" and "Sample 2". The test results show that the towels containing the most absorbent composition held the most water.

TABLE II

| Absorbent Composition in the Sheet (Grams) | VFS Absorption (Grams) | |
|---|---|---|
| | Sample 1 | Sample 2 |
| 0 (Blank) | 35.9 | 36.3 |
| 0.1 | 41.7 | 39.4 |
| 0.2 | 42.7 | 41.6 |
| 0.3 | 44.4 | 46.4 |
| 0.4 | 46.1 | 44.4 |
| 0.6 | 50.5 | 46.6 |

The absorbent composition disclosed herein can be applied to other absorbent articles including, but not limited to: catamenial devices, disposable diapers, incontinent briefs, or bedliners. The absorbent composition will work in any article used to absorb large amounts of liquid and hold them under pressure. In catamenials, the absorbent composition would be located in an absorbent core. In disposable diapers or in incontinent briefs, the composition disclosed herein may be incorporated into the absorbent core between a topsheet and a backsheet to absorb and hold liquid, i.e., body extrudates, under pressure.

It will be understood by those skilled in the art that the composition and articles of this invention have been described with reference to exemplary embodiments and that variations and modifications can be effected in the described embodiments without departing from the scope and spirit of the invention.

What is claimed is:

1. An absorbent composition comprising a copolymer of acrylic acid cross-linked with a first cross-linking component comprising a monomer having at least two vinyl groups and a second cross-linking component comprising an ionic divalent cation.

2. The composition of claim 1 wherein the acrylic acid is neutralized with sodium hydroxide.

3. An absorbent composition having a formula of:

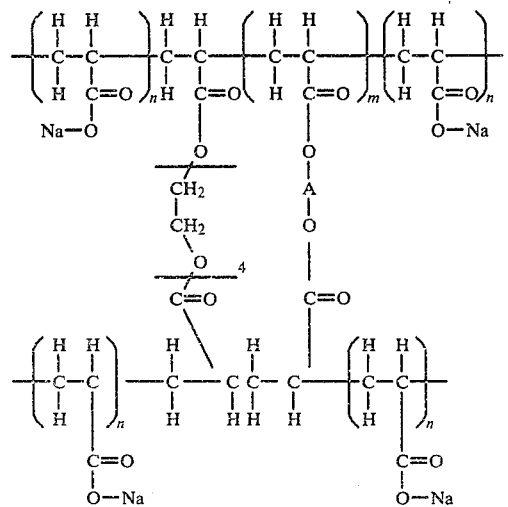

where n is approximately 100–500; m is approximately 1–30; and A is selected from the group consisting of zinc, calcium, barium, strontium, or mixtures thereof.

4. The composition of claim 1 additionally containing cellulose fibers mixed therewith.

5. The composition claimed in claims 1 or 3 wherein the copolymer contains up to 50% by weight of a fourth component selected from the group consisting of methacrylic acid, 2-hydroxyethyl methacrylate, acrylamide, acrylic esters and mixtures thereof.

6. The composition as claimed in claims 1 or 2 or 3 wherein the second cross-linking component is zinc and comprises 6 to 30% by weight of said composition.

7. The composition as claimed in claim 6 where zinc comprises 10 to 12% by weight of said composition.

8. The composition as claimed in claims 1 or 3 wherein the second cross-linking component is calcium and comprises 3 to 8 weight percent of said composition.

9. The composition as claimed in claim 8 wherein calcium comprises 6 to 7 weight percent of said composition.

10. The composition as claimed in claim 1 wherein said second cross-linking component is strontium and comprises 8 to 18 weight percent of said composition.

11. The composition as claimed in claim 10 wherein strontium comprises 10 to 16 weight percent of said composition.

12. The composition as claimed in claim 1 wherein said second cross-linking component is barium and comprises 12 to 28 percent by weight of the composition.

13. The composition as claimed in claim 12 wherein said second cross-linking component is barium and comprises 16 to 25 percent by weight of the composition.

14. The composition as claimed in claim 3 wherein A is a mixture of zinc, calcium, strontium and barium.

15. A process to make an absorbent polymeric composition comprising:
supplying to a container means acrylic acid, a cross-linking monomer having at least two vinyl groups, potassium persulfate and water;
forming a first mixture by mixing the contents of said container means in a nitrogen atmosphere at approximately 40°–80° C. for approximately one hour;
maintaining said first mixture in the container means at 40°–80° C. for approximately two hours;
neutralizing said first mixture to yield a second mixture; and
adding ionic divalent cation to said second mixture and mixing to yield a third mixture.

16. The process as claimed in claim 15 wherein the cross-linking monomer selected from the group consisting of tetraethylene glycol diacrylate, ethylene glycol diacrylate and diacrylamide.

17. The process claimed in claim 15 wherein the ionic divalent cation is selected from the group consisting of zinc, calcium, barium, strontium and mixtures thereof.

18. The process as claimed in claim 15 wherein said first mixture includes a second monomer selected from the group consisting of methacrylic acid, 2-hydroxyethyl methacrylate, acrylamide, and mixtures thereof.

* * * * *